United States Patent [19]

Dolezal

[11] Patent Number: 5,042,910
[45] Date of Patent: Aug. 27, 1991

[54] PRISMATIC IMAGE TRANSPOSING OPTICAL SYSTEM

[76] Inventor: Hubert Dolezal, 1960 Lincoln Park West, Chicago, Ill. 60614

[21] Appl. No.: 405,148

[22] Filed: Sep. 7, 1989

[51] Int. Cl.$^5$ .................. G02B 23/02; G02B 23/18; G02B 5/04; G02B 7/18
[52] U.S. Cl. .................. 359/480; 2/428; 359/831
[58] Field of Search ........... 350/145, 286, 287, 276 R; 2/426, 428, 432, 436

[56] References Cited

U.S. PATENT DOCUMENTS

| | | |
|---|---|---|
| 1,027,576 | 5/1912 | Victor . |
| 1,850,153 | 3/1932 | Paroselli . |
| 2,123,682 | 7/1938 | Wingate . |
| 2,194,192 | 3/1940 | Auer . |
| 2,594,698 | 4/1952 | Thomas . |
| 2,618,199 | 11/1952 | Evans . |
| 2,955,156 | 10/1960 | Heilig . |
| 3,039,351 | 6/1962 | Spagna et al. . |
| 3,655,264 | 4/1972 | Pickett . |
| 3,787,688 | 1/1974 | Stone . |
| 4,077,703 | 3/1978 | Pablo . |
| 4,353,621 | 10/1982 | Geer et al. . |
| 4,435,852 | 3/1984 | Nesler . |
| 4,447,914 | 5/1984 | Jannard . |

OTHER PUBLICATIONS

"Ways to Use Electronics in Design", Design News, Aug. 6, 1984.
"Living in a World Transformed, Perceptual and Performatory Adaptation to Visual Distortion", Hubert Dolezal, Academic Press 1982.

Primary Examiner—Jon W. Henry
Attorney, Agent, or Firm—Willian Brinks Olds Hofer Gilson & Lione

[57] ABSTRACT

A lightweight optical system is provided for enabling a person wearing such system to transpose viewed images. The apparatus comprises a removable, elongated, lighter than glass prism mounted in a lightweight frame which fits snugly on the face and is secured by a strap. The frame includes light occluding elements which prevent substantially all untransposed light from entering the eyes of the wearer.

26 Claims, 4 Drawing Sheets

PRISMATIC IMAGE TRANSPOSING OPTICAL SYSTEM

BACKGROUND OF THE INVENTION

The present invention relates generally to an optical system and more particularly to a lightweight optical system which may be worn on the head for transposing viewed images.

Image transposing devices have been used in the psychophysical and behavioral effects of many forms of motion sickness. Such devices produce a reversal of compensatory eye movements. Wearing such an image transposing device may create motion sickness symptoms These symptoms include, for example: 1) dizziness; 2) vertigo; 3) flushing; 4) sweating; 5) excessive salivation; 6) pallor; 7) dryness of mouth; 8) tachycardia; 9) stomach awareness; 10) stomach discomfort; 1) queasiness; 12) vomiting; 13) spatial disorientation; 14) fine and gross motor incoordination; 15) disequilibration; 16) misreaching; 17) tremor; 18) temporary cognitive deficits; and 19) short-term memory problems.

The study of such symptoms is particularly important since a combination of several of these symptoms may provide researchers with an ability to simulate the combination of symptoms which appear in some human disorders. For example, symptoms 13 through 19 listed in the preceding paragraph are equivalent to Parkinsonism-like effects. Similarly, symptoms 1–18 may be observed and simulated by researchers investigating space motion sickness, airsickness, seasickness, and ground-motion sickness. The device allows use by animal subjects, e.g., rethesusi or macaque monkeys.

Another aspect of the research involving the use of image transposing devices is investigating the ability of subjects to adapt to the symptoms caused by wearing such an image transposing device.

Several image transposing systems are available in the art. Presently available image transposing devices, however, have several deficiencies for use as a research tool. Some of the major disadvantages of presently available systems are discussed in detail below. Briefly, presently available image transposing systems are either large and heavy, do an inadequate job of blocking untransposed light, have small fields of view, or other inadequacies.

Systems similar to the system shown in U.S. Pat. No. 2,123,682 (Wingate) are housed in spectacles and thus do not block untransposed light. Thus, such systems are not effective in preventing untransposed light from reaching the eyes. That is, some light enters the eyes which has not first passed through the prisms. Such systems are unreliable from an experimental point of view since any effects the wearer experiences cannot necessarily be attributed to viewing transposed images.

Other systems such as the one disclosed by Dolezal in the book *Living in a World Transformed*, Academic Press 1982, includes a glass prism for transposing images and a helmet as a prism retaining device. This system weighs over 8 pounds placing great strain on the neck of the wearer. The system requires a counterweight to offset the weight of the heavy glass prisms and the heavy prism housing and helmet. In addition, this helmet and counterweight system increases the dimensions of the head by over 50% in all directions which may cause the wearer to unintentionally run into objects with his or her head.

Furthermore, the prism in systems similar to the helmet system described by Dolezal in the above-referenced book often fog up and/or require application of anti-fogging fluid. The fogging in such systems is due to inadequate air circulation around the prism.

Although prisms made of materials such as acrylic are known, such acrylic prisms have been adequate for use in image transposing systems used in psychological studies. Although available acrylic prisms are lightweight they have disadvantages. The most significant problem with prisms made of acrylic or other nonglass materials is the unacceptable level of the optical flatness of the prism. The best available prisms made of a lighter-than-glass material have a surface flatness from 200–400 waves as measured under sodium light. Images seen through these prisms appear blurred and "wavy."

Previously known image transposing devices have other disadvantages. For example, the device disclosed in U.S. Pat. No. 3,039,351 (Spagna) utilizes two prisms. In addition to having a complicated construction, such two-prism devices are prone to cause binocular disparity (double images). The binocular disparity in such systems is caused because of the use of two separate prisms or lenses, one for each eye. Even a slight shift of the prisms creates the double images. As will be recognized by those skilled in the art, binocular disparity defeats the purpose of the device when used as a research tool, viz., clear vision.

Systems such as that shown in U.S. Pat. No. 4,077,703 (Pablio) have very restricted fields of view. Such image transposing devices severely limit or restrict the normal scope of human peripheral vision, thus limiting the usefulness of the device in any use that depends upon or is improved by a large field of view. A restricted field of view is undesirable since it makes performing tasks difficult. This disadvantage is especially significant from an experimental point of view since the effects of viewing transformed images cannot be separated from the effects of a very restricted field of view.

Another image transposing device is disclosed in U.S. Pat. No. 4,353,621 (Geer). Devices such as the one disclosed by Geer must be held in front of the eyes of the user with one or both hands. Thus, the use of one or both hands is obviated in performing desirable or necessary eye-hand coordinating tasks. In addition to limiting the user's ability to perform normally, the user's physical safety may be compromised if holding on or steadying should become necessary when balance is lost.

Another disadvantage of previously known image transposing devices is that the distance from the eyes of the viewer is either fixed and relatively distant or quite unreliably variable and is not alterable (cannot be adjusted). In some available systems, once the prism(s) is (are) fixed in its (their) frame the prism(s) cannot be quickly removed or exchanged, thus making expeditious cleaning impossible. Expeditious cleaning may be particularly important in instances where the wearer continues to wear the frame of the goggles. Further, if the prism(s) is non-adjustable in the frame, the prism(s) cannot be adjusted for distance, slope, and/or angle relative to the user's eye or head posture.

Further, image transposing devices usually include prisms which have a relatively sharp prism edge which can abut the nose of the viewer. This sharp edge has several disadvantages. First, the sharp edge can create irritation or damage to the nose. Further, the sharp edge necessarily limits how close the prism can be moved to the eyes. Finally, the sharp edge renders the scope of the field of view of each viewer variable as a function of that individual's nose size. That is, the scope/size of the field of view of different wearers will be different. Thus, any precise between-subject comparisons in experimental paradigms that seek to compare subject performance characteristics are invalidated.

Therefore, in view of the above, it is a primary object of the present inventions to provide an image transposing system which may be worn for extended periods of time without influencing the symptoms caused by the image transformation.

It is a further object of the present invention to provide a lightweight image transposing system.

It is a further object of the present invention to provide an image transposing system which obviates binocular disparity.

It is another object of the present invention to provide an image transposing system which maximizes the scope of peripheral vision of the wearer.

It is a further object of the prevent invention to provide an image transposing system which yields reliable inter-subject comparisons by permitting comparable field of view size for different subjects.

It is a further object of the present invention to provide an optically flat polymer surface. creating clear visual images.

It is still a further object of the present invention to provide an image transposing system that permits easy adjustment and removal or exchange of the system's prism(s).

SUMMARY OF THE INVENTION

To achieve the foregoing objects and in accordance with the purposes of the present invention the image transposing optical system of the present invention may comprise frame means for securing the frame to the head of the wearer, and an elongated prism made of a lighter than glass material having an optically flat surface measuring less than 40 waves. The system further includes light occluding means for presenting substantially all untransposed light from entering the eyes of the wearer.

In a preferred embodiment of the present invention, the image transposing optical system combines the essential qualities of blocking all untransposed light while being very light in weight and small in size. In addition, the system has a large field of view and leaves the hands free.

Additional objects, advantages and novel features of the invention will be set forth in part in the description which follows, and in part will become apparent to those skilled in the art upon examination of the following or may be learned by practice of the invention. The object and advantages of the invention may be obtained by means of the combinations particularly pointed out in the appended claims.

BRIEF DESCRIPTION OF DRAWINGS

FIG. 1a is an exploded view of the image transposing optical system illustrated in FIG. 1

DETAILED DESCRIPTION OF THE PRESENTLY PREFERRED EMBODIMENTS

Figure 1:
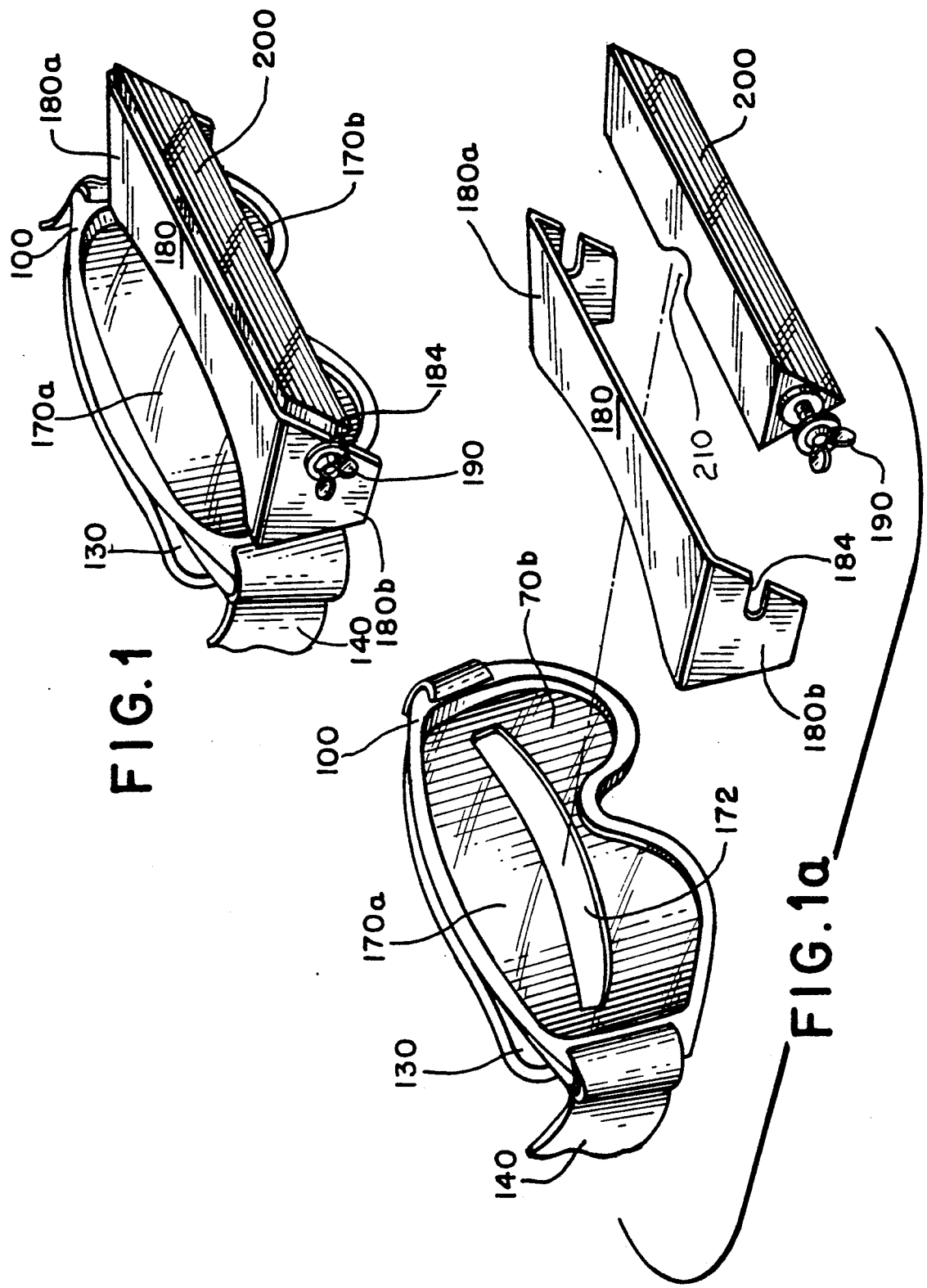
FIG. 1 is a perspective view of a preferred embodiment of a prismatic image transposing optical system of the present invention.

The following description of the preferred embodiments will be made with reference to the drawings wherein like elements are referred to with like reference numerals throughout the various views. Referring specifically to FIGS. 1 and 1a, a preferred embodiment of the prismatic image transposing optical system of the present invention is illustrated. The structure comprises frame means in the form of a goggle frame 100. The frame 100 is preferably similar to the frames used in a ski mask of the type which uses a lightweight opaque plastic or rubber.

Figure 2:
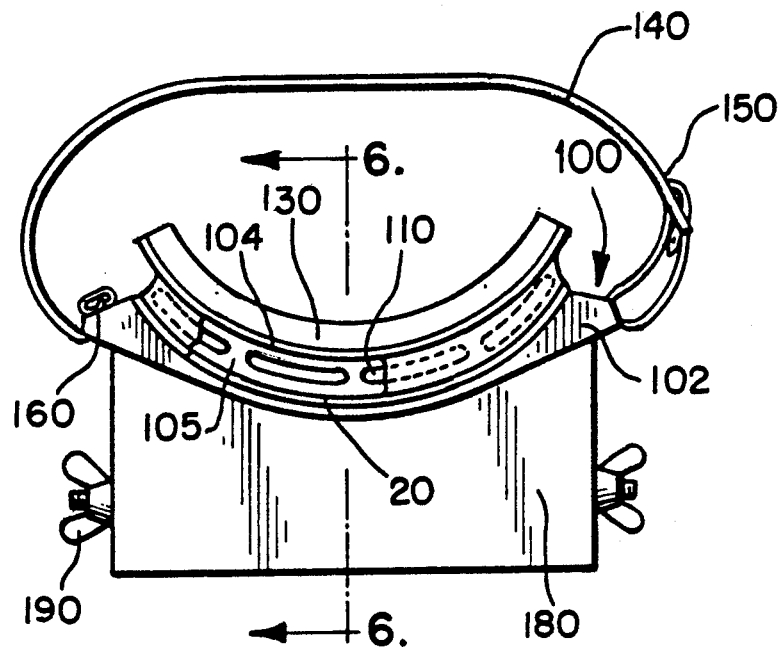
FIG. 2 is a top view of the system illustrated in FIG. 1.
Figure 3:
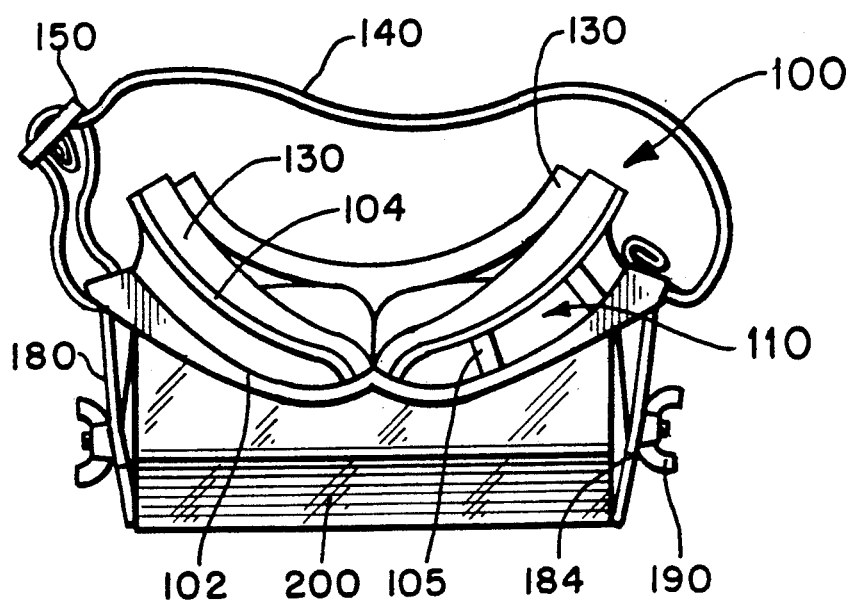
FIG. 3 is a bottom view of the system illustrated in FIG. 1.
Figure 6:
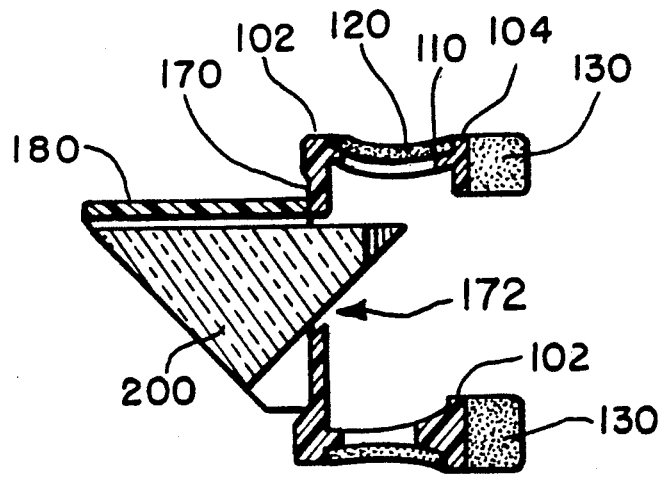
FIG. 6 is a cross sectional view of the system taken along line 6—6 of FIG. 2.

As best illustrated in FIGS. 2, 3 and 6, the goggle frame 100 comprises a front rim 102 and a back rim 104. The back rim 104 conforms generally to the contour of the face of a human wearer. A plurality of ribs 105 connect the front rim 102 to the back rim 104. A plurality of slits 110 are defined between the ribs 105.

Figure 8:
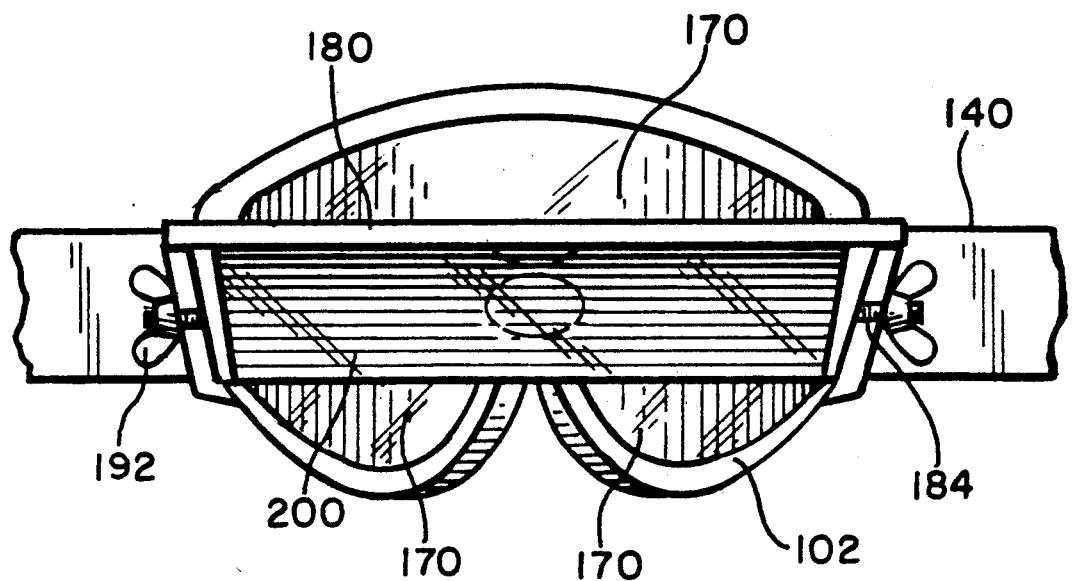
FIG. 8 is a front view of the system illustrated in FIG. 1.

A prism housing 180 is attached to the front of the frame 100 by epoxy or some other suitable method. Preferably, prism housing 180 is made of a suitable lightweight opaque material such as plastic. As illustrated best in FIGS. 1a and 3, the prism housing 180 includes a top section or plate 180a and two side sections or plates 180b, one on each side of the frame 100. As illustrated in FIGS. 1a and 8, the housing 180 is preferably open on the front, bottom, and back. Thus, the prism 200 is covered by the housing 180 to block light from the top and sides of the prism 200.

An elongated prism 200 is made of a lighter than glass material. Preferably, the elongated prism 200 is made of some lightweight transparent material such as a transparent polymer and more preferably made of acrylic. The elongated prism 200 is suspended inside of the prism housing 180 by a prism retainer assembly 190.

In the embodiment shown, the prism 200 is a right angle 45°×45°×90° prism. Preferably, the prism 200 extends the length of the frame 100 and is longer than the distance between the eyes of the wearer. For example, the prism 200 may be approximately 49 ×49 ×67 mm. The prism 200 is preferably arranged in the frame 100 such that the hypotenuse of the prism 200 is perpendicular to the plane which contains both of the eyes of the wearer and such that the apex of the hypotenuse forms a line parallel to the plane which contains both of the eyes. The prism 200 preferably includes a nose notch 210 which is defined by a depression cut into the edge of the prism 200. The depression is formed deep and wide enough to accommodate the bridge of the nose of the wearer.

As best illustrated in FIG. 1a, curved face plate 170 is configured to cover the area inside of the goggle frame and includes an aperture or slot 172. The slot 172 extends laterally across the width of the frame 100 from approximately one side of the frame to the opposite side of the frame 100. The slot 172 is disposed such that the eyes of the wearer are level with the slot 172. The face plate 170 includes a top portion 170a above the slot 172 and a lower portion 170b below the slot 172. The face plate 170 may be attached to the front rim 102 of the frame 100 and prism housing 180 by epoxy or suitable method. The face plate 170 is preferably made of a lightweight opaque material such as an opaque plastic. Thus, the face plate 170 occludes untransposed light.

A face seal 130, preferably made of foam rubber or some other lightweight flexible opaque material, is attached, by epoxy or similar method, to the back rim 104 of the frame 100. The face seal 130 extends around the entire perimeter of the back of the frame 100. As discussed above, a plurality of ribs 105 connect the front rim 102 to the back rim 104 such that the frame 100 contains a plurality of slits which act as vents 110. The slits 110 are preferably covered by a thin fabric covering 120 which functions to block light. The covering is preferably made of foam rubber or some other lightweight porous opaque material and functions to block light from entering the vents 110.

An adjustable strap 140 is connected to the back of the frame 100 by suitable means. In the embodiment shown in the figures, the strap 140 is connected by means of a strap holder 160. The strap holder 160 comprises a slit on each of the ends of the frame 100 such that a rib is defined. The strap 140 is looped around the rib. Preferably, a length adjustor 150 is provided along the length of the strap 140.

Figure 7:
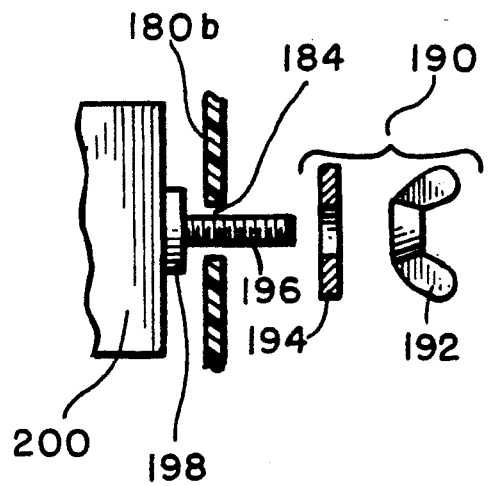
FIG. 7 is an exploded view of a preferred embodiment of the prism retaining assembly.

Now referring to FIG. 7 an exploded view of a preferred embodiment of the prism retainer assembly 190 is illustrated. The retainer assembly 190 includes a bolt 196 which extends through a slot 184 formed in the side sections 180b of the prism housing 180. Preferably, the head of the bolt 198 is attached to the prism 200 with epoxy. The bolt 196 is secured to the prism housing 180 by a washer 194 and wing nut 192.

Other modifications may be made to the system of the present invention depending on the particular use contemplated.

For example, other embodiments include replacing the right angle prism with other shapes and orientations of prisms. Also, the frame may be modified in such a manner that the system could be worn by animals rather than humans. In addition, a light filter may be added to the prism, most easily done by inserting the filter into a groove in the prism housing in front of the prism.

In other embodiments the system may include bellows or some other suitable device between the prism housing and the face plate which allows the prism to be rotated to different positions. Alternatively, the housing itself could be modified to allow rotation of the prism including motorized rotation along any axis of tilt or rotation.

GRINDING AND POLISHING OF PRISMS

As discussed above, in order for the device of the present invention to function, the optical flatness of the prism must be below 40 waves and preferably about 20 waves. The following is a description of a new method of grinding and polishing for a polymer, such as acrylic which results in the desired flatness for the prism 200 of the present invention.

GRINDING AND POLISHING

As a first step, a square stock of a polymer material is cut on a 45 degree angle to make two prisms. Preferred materials are acrylic resin (M-96); styrene resin (M-80); or lexan polycarbonate (M-70). After the block is cut the second step is to machine the cut prism surfaces making them mechanically flat. The cut prism may be machined by using a milling machine which includes a fly cutter or using sanding belt and/or disk.

The first step in the process, after the prisms have been cut is the grinding step. The cut prisms are processed by first grinding with (untreated) silicone carbide (carborundum—CSi) on a steel (cold rolled) lapping plate or an aluminum/ceramic tile plate. In the grinding process, silicone carbide materials of progressively decreasing grit structure are used. The following sequence grit structures is preferred: a) 60 grit (60 grains per inch—American Standard sieve sizes); b) 80 grit; c) 120 grit; d) 220 grit; e) 320 grit (aluminum/ceramic tile plate optional); f) 400 grit (aluminum/ceramic tile plate optional); g) 600 grit (24 microns) use on aluminum/ceramic tiled plate (mechanically flat) or steel plate machined flat to 3/1000ths of an inch and used with nothing heavier than 220 grit.

After the above grinding procedure, the prism is subjected to a microgrit fine grinding (pre-polish) step. The microgrit fine grinding step includes grinding the prism with materials having a grit size at the micron level such as (untreated) aluminum oxides (AL203). Preferably the polishing materials in this step are applied on a glass plate (mechanically flat), aluminum/ceramic tile plate (mechanically flat), or steel plate machined flat to 3/1000ths of an inch and used with nothing heavier than 400 grit. A preferred succession of grit sizes is: a) 17.5 microns; b) 9.5 microns; c) 3.0 microns; and d) 1.0 micron (optional).

After the micro fine grinding step, the prism is polished with Pellon Pressure Sensitive cloth. The pressure sensitive cloth may be, for example, #61 light—color: light brown; nap of cloth extremely small preferably glued to a glass plate (mechanically flat) or steel plate machined flat to 3/1000ths of an inch and used with nothing larger than 600 grit with #1600 cerium oxide (fast polish) 1-3 microns (crystals have flat surfaces).

After using the existing application of #1600 solution for about one hour (on all three sides of prism), no new #1600 solution is applied. Instead, the existing #1600 solution on the nap of the cloth is used for another 1-2 hours on all three sides of the prism. After thirty to forty-five minutes of utilizing an extended use of #1600, the 1-3 micron (flat crystals) break down to about 0.5-1.0 microns (flat crystals) and the prism surface will become 3-5% clearer with thirty to sixty minutes of continued polishing. Preferably the three prism surfaces receive equal polishing time. The "broken down" #1600 solution is continuously returned to the polishing pad that accumulates on the prism's faces. One of the prism edges may be used to "pull" the dispersed #1600 solution spread over the 12 inch polishing pad back to the center. When the #1600 solution begins to "dry out" (becomes a little pasty) a few drops of water (a separate uncontaminated plastic container of plain water must be used for this purpose) is added to the center of the polishing pad.

The prism is then be polished with red rouge ½ micron.

Any grit which is larger than the one you are polishing with will mar, cut, or scratch the surface if the larger grit comes in contact with the prism's surfaces while handling, grinding, or polishing it. Therefore, the cleaning and washing of the tool is extremely important. Both sides of the tool, including the rings on steel or aluminum plates and in between the tiles of a ceramic tiled plate, must be cleaned such as by scrubbing with a small hand brush to remove all grit. A brush such as a toothbrush may be especially helpful when cleaning tool(s) and in between the blocked prisms. Several washings are preferred before moving on to a smaller grit size.

Different areas should be utilized for grinding and polishing. The grinding area should consist of grit sizes 60 to 600. The microgrit fine grinding area should be limited to 24 to 1 micron size grains. The polishing area, which uses #1600 cerium oxide (fast polish) should be in a separate room or a cleansed microgrit fine grinding area.

Grit ranging from 24 to 1 micron is available as a powder/dust, which when coming in contact with the air by filling plastic containers/bottles and during polishing, settles on all areas. If the work area and tools become contaminated with larger grit sizes, then everything should be washed (especially hands and tooling). It will be recognized by those skilled in the art that working in grinding and polishing areas simultaneously should be avoided, since grit will cling to clothes, hair, and hands contaminating work areas and could possibly mar, cut, or scratch the polished surfaces.

Grit sizes 60 to 400 should be placed in containers having one to three-sixteenth inch holes. Grit sizes 24 microns to 1-3 micra (#1600 cerium oxide) are preferably placed in plastic bottles preferably having a small spout. All containers should be washed and rinsed thoroughly before filling with grit. As an example the solution may be prepared as follows. A plastic bottle (1 quart or less in size) is filled with three to five tablespoons of grit (depending on container size) and filled one-third with water. When ready to use, the bottle should be shaken.

Contamination of grit canisters due to unwashed hands, unclean container/bottles, and soiled spoons; and open canisters and/or spilled grit will result in immediate disposal of grit. Therefore care should be taken to avoid such contamination.

The edges of the plastic prisms (and glass plates) will become sharp after grinding or polishing for a while, especially when using 60 to 400 grit. To avoid chipping the edges of the plastic prisms (and glass plates) while polishing, a coarse sharping stone may be used to chamfer the edges. Care should be taken to prevent the sharping stone and resulting grit from rubbing against the polished surfaces. Immediately after filing, the polished surfaces are preferably washed or rinsed off with running water (several times if necessary).

The edges of a prism can also be beveled by rubbing the prism edge(s) against the tool's surface moving back and forth, left to right, or in a circular motion.

All tools tend to become concave (hollowed out in the middle) over a period of time due to several factors. First, the grit size plays a critical role in wearing down and reshaping the surface of the tool. For example, 80 grit will cause a more rapid abrasion of tooling surface into a concave pattern. Third, the kind of tool is also important to consider. For example, a glass tool tends to wear at a faster rate than a steel tool. Fourth, a tool used more on a machine than by hand will tend to become concave at a faster rate, especially if that tool is an aluminum plate or an aluminum ceramic tiled plate. Fifth, the amounts of pressure and types of movement and rotation of the polisher and the blocked plate of four prisms or individual prisms on the tool will "shape" its surface.

In order to bring the tooling back into play as a "useable" instrument each tool must be ground and/or polished against each other. A tool is only "usable" when it is maximally flat. The degree of concavity will determine the size of grit used. The deeper the concavity, the larger the grit size. Usually 220, 320, or 400 grit may be used to start with. However, 600 grit may be started with if the surface is slightly concaved and then Microgrit Fine Grinding steps can be used if necessary. Generally, a larger grit size should be used at the outset to bring the tool down to a non-concave point. Finally, the material having a grit of 3.0 or 1.0 microns is used to smooth and flatten the tool to a suitable stage of usage. As the concavity shrinks in size, the grit size should be reduced as well. Finally, the tool should be tested under sodium light against a master flat (optically flat glass plate). Problem areas should be noted and can be marked.

The prisms may be processed either by techniques using a blocking plate or the prisms may be individually processed.

Preparing Prisms on Blocking Plate

A blocking plate having four sets of slots into which the prisms (ca. 164mm length) are placed into is preferably used. The blocking plate positions three of the prisms parallel with one another while the fourth prism is placed perpendicular to the other three. The prisms are affixed such as by being glued into place using heavy duty double stick tape or hot pitch. When grinding/polishing, the hypotenuse side (ca. 65mm) is placed up and each slot holds one prism. After the hypotenuse side is polished to 3.0 microns, the prisms are removed from their respective slots. The hypotenuse side is rinsed/washed, dried with paper toweling and/or tissue, and then covered, preferably with 2" wide masking tape to protect its surface from coming into contact with larger grit sizes.

Now the right angle sides are to be ground/ polished to 3.0 microns. The prisms are then preferably paired into two slots with the molded (right angle) sides (ca. 45mm) of each pair placed adjacent one to another. The prisms are placed into the two opposite end slots of the blocking plate. In order to ensure even grinding/polishing, the two pairs of prisms in the two opposite slots should extend about 1-2 inches out of their respective slots away from the slot perpendicular to the three slots, and a keeper (counter weight) be inserted in the center of the slot perpendicular to the three parallel ones by using heavy duty double stick tape or hot pitch. To grind/polish the molded (second right angle) side, the prisms are removed, rinsed/washed, dried, and then covered with 2" wide masking tape. The processed right angle sides of the prisms are then placed adjacent to one another (like the molded sides) and placed as a pair into the two opposite end slots on the blocking plate. Since the molded sides are relatively level and smooth, the grinding/polishing may be started with 400 grit. The molded sides must be covered with masking tape before any grinding takes place to protect it from excessive scratches and deep marring.

To ensure even grinding and polishing repeat the same method as used with the non-molded prism sides by extending the two pairs of prisms out about 1-2 inches and placing a keeper in the slot perpendicular to the three parallel ones. The sides are to be ground/polished to 3.0 microns. Each time the prisms are removed from the blocking plate, the blocking plate, keeper, and prisms should be rinsed/washed thoroughly several times.

A tool such as a toothbrush may be used to remove grit that is inaccessible without the aid of some small cleaning device where edges, corners, grooves, gaps, or hard to reach areas hold grit.

After rinsing/washing the blocked prisms and removing them from the blocking plate, the individual prisms should be thoroughly rinsed/washed and dried with paper toweling and/or tissue. The empty blocking plate should be thoroughly rinsed/washed with a small hand brush and dried with paper toweling and/or tissue before resetting another batch of prisms into the blocking plate slots again.

After the three sides of the blocked prisms are polished to 3.0 1.0 microns the masking tape is removed from sides of the prism, then they must be thoroughly rinsed/washed again but very carefully.

The prisms are then individually polished using the 1.0 micron step before proceeding to the polishing stage.

Application of Grit to Tool

When grinding with 60 to 400 grit on a steel and/or aluminum/ceramic tile plate, the grit (¼ to ½ of a teaspoon) is preferably sprinkled over the surface of the tool. Grit size 600 may be sprinkled and/or used in solution form being applied by squirting a small puddle on the center of the tool. A container filled with plain water is used to squirt a small puddle into the center of the tool to act as a lubricant between the prisms, grit, and tooling. As the blocked prisms are being rotated in a back and forth and/or circular motion the grit spreads over the tool's surface. Both the grit and water solution tends to run off the edges of the tool's surface and should be continuously reapplied. The larger the grit size in use the more reapplication will be necessary. The need to reapply more water, grit and/or grit solution will depend on the length of time grinding, the amount of pressure on the prisms, and the grit size. The prism's surfaces should be thoroughly rinsed/washed after each grinding step.

When polishing with aluminum oxide (17.5 to 1.0 microns) on a steel, glass or aluminum/ceramic plate the grit in the container should be shaken and then squirted on the tool's surface covering the inner half of it. As the blocked prisms are being ground back and forth and/or in a circular motion the grit (suspended in water) will spread over the tool's surface. It may be desirable that the blocked prisms, when being polished, should meet with greater resistance. The reduction of grit size through polishing, the addition of "new" grit to the tool, and especially the evaporation of water of the tool's surface increases the amount and degree of polishing. The prism's surfaces should be thoroughly rinsed/washed after each microgrit fine grinding step in order to inspect them, judge the progress, and avoid contaminating the next step in the process.

When polishing with #1600 cerium oxide an/or red rouge on a polishing cloth (nap of cloth extremely small) glued to a steel or glass plate, the grit in the container should be shaken and then squirted on the cloth's surface covering most of it. As the individual prisms are being polished (using several different methods of movements and rotations) the grit solution is absorbed by the cloth and spreads throughout its surface. The grit solution quickly will tend to run off the edges of the tool and/or dry up when polishing for about 15 minutes or less (the individual prisms will get harder to move around as the polishing continues). Therefore, the individual prisms should be moved to the side of the tool (be careful not to scratch the prisms against the edge of the tool) and the grit solution should be reapplied by squirting a small puddle in the center of the cloth. Sometimes it is desirable that the individual prism, when being polished, should meet with greater resistance by polishing for a longer period of time before adding new grit solution. The reduction of grit size through polishing, and especially the evaporating of water off the tool's surface increases the amount and degree of polishing. The prism's surfaces should be thoroughly rinsed/washed after this final polishing step in order to inspect them, judge the results, and prepare them for usage.

Gripping and Holding Prisms

When the prisms are blocked, the blocking plate is preferably moderately gripped along the outer perimeters with thumbs on top and the other finger holding the under side of the plate.

The individual prisms may be held in three different ways. First, a single prism can be gripped at the both ends with the three fingers from each hand. Second, the single prism can be held from the top with both hands (fingers pressing on its sides) several inches from the center. Third, the single prism can be gripped from the sides (fingers pressing) with the hands almost parallel with the prism. A firm gripping and holding pattern of the prisms prevents them from "rocking," thus ensuring even grinding/polishing.

Movement and Rotation of Polisher and Prisms

When the prisms are blocked, the blocking plate should be moved in diverse directions and rotations for even grinding/polishing and even tooling wear. The movements of the blocking plate can be away and toward (back and forth from) the polisher, left to right (side to side) of the polisher, and/or in quarter turn concentric circles covering the whole tool with the polisher in a stationary position.

Grinding/Polishing Individual Prisms

The individual prisms should be moved in diverse direction and rotations for even grinding/polishing, tool, and cloth wear. The movements of the individual prisms depends largely on the type of gripping/holding method described above. The first method wherein the prism is gripped at both ends allows movement of the prism from left to right (side to side) of the polisher or away and toward (back and forth) from the polisher. This method is very useful for polishing and repolishing of all prism sides. The movements and rotations of the prism should embody the whole area of the tool and cloth. A variety of movements and rotations covering the expanse of the tool and cloth will make the best use of the grit solution, the tool, and the nap of the cloth producing a flatter surface.

Pressure of Polisher on Prism

The weight of the blocking plate and the exertion of pressure and movement by the polisher on the grinding-/polishing side of the prisms will determine the amount of time spent grinding/polishing and the frequency of grit applications. The larger the grit size the less water or solution or pressure needed to grind/polish. The smaller the grit size the more pressure may be exerted to decrease grinding/polishing time.

Because of the small grit size, subsequent reduction of grit size due to polishing time length, and reapplication of water and grit solution, the pressure produced under normal (gripping/holding and movement/rotation) conditions is adequate.

Maintaining Uniformity of Individual Prisms

In the first area of prism uniformity the width of each side of the prism should be the same width from one end of the prism to the other. When a two inch square of acrylic stock is cut on a 45 degree angle resulting in two prisms, the hypotenuse sides will be uneven due to saw blade marks and a small degree of angle error. For example, a prism unevenly cut (1-2mm or less) may be wider on the right end of the hypotenuse face than the left end, thus the two edges of the hypotenuse side should be slightly beveled and the wider side reduced through microgrit fine grinding and/or polishing. The beveled edge(s) should be tapered; that is, the edge should be rounded more at the wider end and gradually decrease as it approaches the narrower end. This is accomplished by polishing with 24 (600 grit), 17.5, 9.5, or 3.0 microns depending on the variance of width of the two opposite ends of the hypotenuse face; polishing the wider end more (the wider half rests on the tool while the narrower half lies off the tool) than the narrower end; polishing the wider end using added pressure (pressing down on the wider half only) and letting the narrower half lightly touch the tool. Caution must be used when beveling the edges of a prism. The polisher does not want to bevel the edge so much at 24, 17.5, or 9.5 microns that one cannot bring back its sharp edge when finishing a prism at 3.0 micron, 1.0 microns, and the #1600 polishing step. The hypotenuse face can then be polished with the same and/or smaller grit size used to bevel the edges; however, the prism should be rinsed/washed thoroughly before proceeding. In order to bring both the right and left ends of the hypotenuse face within the prescribed tolerances of each other, the polisher should grind/polish the wider half more, use greater pressure on the wider end than the narrower end of the prism, and/or use the correct grit size in conjunction with these two polishing methods. These methods will achieve the necessary uniformity to ensure maximum flatness and optical clarity. Each face should be measured often to check for uneven hypotenuse widths. Prism dimensions are usually measured and defined as lengths of face to the intersection of the surfaces. Closely monitoring the hypotenuse face of a prism will ensure greater uniformity of widths, increase the flatness of prisms, and increase the clearness of the prism's surface at the Microgrit Fine Grinding and Polishing stage.

A second area of prism uniformity concerns the angle of the two prism sides each sloped 45 degrees in relationship to the hypotenuse side. In the machining, grinding, and polishing of a prism the angle must be taken into account, not only between the faces which are subsequently to be ground/polished, but also the angle which those faces make to the common base. When a prism contains three or more sides that will be ground and/or polished then there exists the possibility of "pyramidal error," which becomes apparent when in the grinding/polishing stages the base (hypotenuse side) is ground and polished to the prescribed limits of squareness. Pyramidal error is the amount of change in minutes of arc on the slopes of the two prism sides in relationship to the hypotenuse side. To hold optical distortion to a minimum pyramidal error must not exceed 2 minutes of arc on either side. To minimize pyramidal error, prisms should be measured after grinding with 600 grit (24 microns). Location and degree of error should be noted on a prism's sides and/or faces (using water color markers) and corrected (several measurings and microgrit fine grinding—using 17.5 microns—attempts will be necessary). If pyramidal error is beyond 2 minutes of arc, the polisher should continue using 600 grit for about 15 minutes more and then move on to 17.5 microns. When the prisms are at the end of the microgrit fine grinding stage they should be measured again at the 1.0 micron step. If the degree of pyramidal error is less than 2 minutes of arc then the prism can enter the polishing stage. The degree of pyramidal error should be noted (by labeling the sides of the prism with a water color marker) and when using #1600 cerium oxide (1-3 micra) can be held constant or reduced by using various gripping and polishing methods.

Test to determine the flatness may be performed by techniques known in the art such as those similar to the test used by The National Bureau of Standards for testing flatness of optical surfaces by utilizing a monochromatic light source which is usually accomplished with a sodium light source.

OPERATION OF THE SYSTEM

Figure 4:
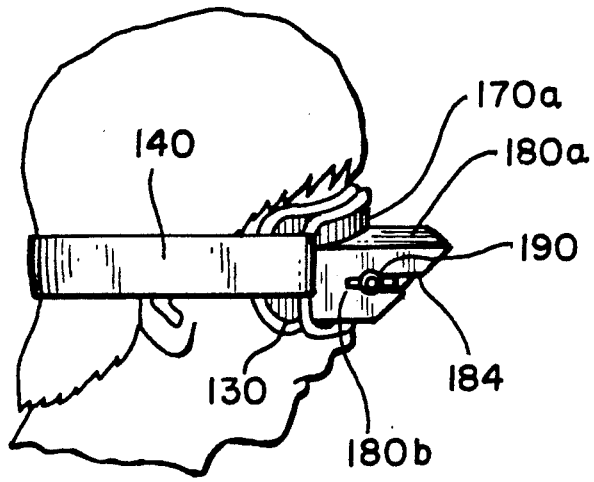
FIG. 4 illustrates the system illustrated in FIG. 1 being worn on a human.
Figure 5:
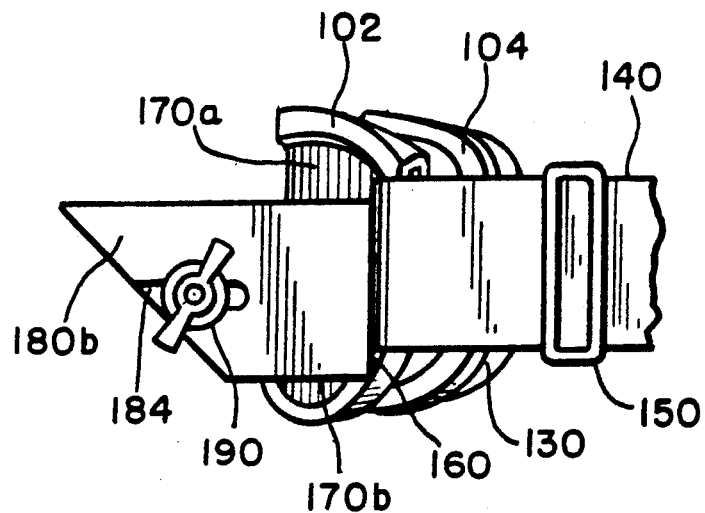
FIG. 5 is a side view of the system illustrated in FIG. 1.

The prismatic image transposing optical system is worn as illustrated in FIG. 4. The strap 140 is placed around the back of the head and tightened by means of the length adjustor 150. The strap 140 is tightened such that the head can be moved vigorously without the system being displaced.

Figure 9:
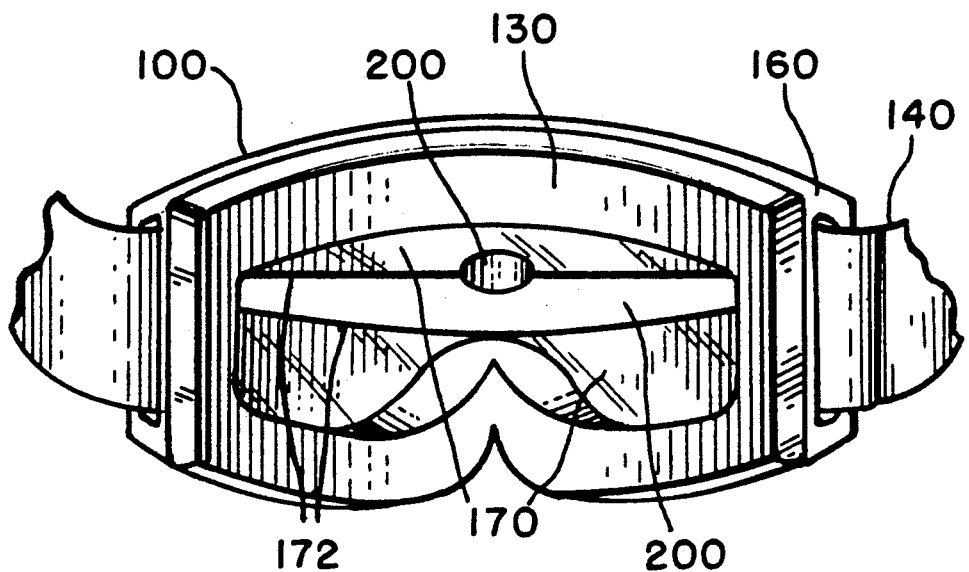
FIG. 9 is a back view of the system illustrated in FIG. 1.

As best illustrated in FIG. 9, the flexible face seal 130 adapts to the contours of an individual's face, forming a snug seal which blocks light from entering.

The eyes of the wearer are positioned behind the lighter than glass prism 200 which extends through the slot 172 in the opaque face plate 170. The bridge of the nose of the wearer rests in the nose notch 210 thus bringing the eyes closer to the surface of the prism and affording a large field of view.

The vents 110 (best illustrated in FIG. 2) allow air to circulate throughout the interior of the frame 100 thus preventing the prism 200 from fogging. The thin layer of porous opaque covering 120 covers the vents 110 to block light from entering through the vents 110.

The prism 200 can be easily removed by loosening the wing nut 192 of the prism retainer assembly on each side of the prism housing 180, and sliding the bolt 196 which is attached to the prism through the slot 184 in the prism housing 180.

When the system is worn, all light reaching the eyes of the wearer passes first through the prism 200 which, in a method generally known, causes images perceived by the eye to be transposed. As will be recognized by those skilled in the art, the manner in which the image is transposed will depend on the dimensions and position of the prism 200. In the embodiment shown, the prism is a right angle prism whose orientation is such that the field of view is reversed in the up-down direction.

The process of grinding and polishing an acrylic prism of the present invention makes it possible to significantly exceed the optical flatness of any large flat acrylic surface known in the art. The standard of optical flatness and hence clarity that is achieved with the disclosed process is reliably and consistently at or below 40 waves and preferably below 20 waves, surpassing the present industry standard of 200 waves by a factor of 10.

The clarity which is achieved using this method is due to the grinding and polishing process described above. It is the combination of having the largest field of view ever achieved with a lightweight prism and creating an optically flat surface that affords visual clarity, which makes the present invention unique.

The prism is lighter and larger and optically clearer than prisms previously used in goggles. Prisms used in goggles previously have been glass. Lightness is important because it substantially improves the comfort level of the wearer. Although acrylic prisms are a known art, the present invention incorporates the first to be used in a goggle.

Furthermore, the light weight of the system is accompanied by a small overall size of the system. Thus the dimensions of the head are not excessively increased when the system is worn, thereby eliminating unintentional collisions of the head with other objects.

The size of the prism used is also unique. Available acrylic prisms which are generally used for entertainment purposes, are smaller than the prism of the present invention. The prism of the present invention is longer than the distance between the eyes of the wearer. The prism of the present invention yields the largest reversed, inverted, or tilted field of view every produced, namely ca. 37° vertical × 115° in the horizontal plane.

In spite of the increased size of the prism of the present invention, the optical clarity of this acrylic prism is roughly equivalent to the finest glass prism produced. Specifically under sodium light, the optical clarity/flatness of the prism of the present invention ranges between 10–40 waves.

The design provides the wearer with comfort and hence with the opportunity for extended use and free use of the hands. The design also provides for lightweight materials to be used which adds to the comfort of the wearer; the entire apparatus weighs ca. 1 lbs (½ kg.). The use of a lighter than glass prism, and the light weight of the system as a whole, relieves pressure on the nose and face caused by excessive weight and eliminates the need for a counterweight.

The nose notch in the prism brings the eyes closer to the prism thus affording an even wider field of view, without sacrificing comfort and adaptability for several research subjects. In addition, only one large elongated prism is used thus also affording binocular vision without the risk of binocular disparity which occurs in improperly aligned multi-prism systems.

The attachment of two bolts—on each end—to the prism provides assembly which can be inserted and removed quickly from its casing, making cleaning and maintenance simple. Furthermore, the slot in the frame allows the bolts attached to the prism to be inserted and secured or removed. The slot permits the prism to be moved close to the subject's nose and eyes such that the field of view is maximized.

The frame is of unique dimensions and shape and therefore permits only reversed light to enter the eyes of the viewer/subject—light which would otherwise confound any (experimental) use, rendering any result invalid. This unique design feature permits valid experimental data to be gathered, unconfounded by right-side up (erect, normal) competing visual images. This feature of reflected and refracted light-blocking in an optical prism device provides significant advantages over available systems. The frame is also equipped with vents which eliminate the fogging of the prism which would otherwise occur.

Thus, the prismatic image transposing optical system of the invention provides the important and desirable combination of being lightweight, small in size, occluding untransformed light, fog resistant. The device is secured on the head, leaving the hands free for other tasks and provides a large field of view.

The device of the present invention may be used as a motion sickness stimulator (whether experienced on land, in the air, on water, or in the microgravity of space) as it has those effects when worn; the device may also be used to improve various forms of motion sickness, equilibrium, spatial orientation, and speed and precision of small and gross eye-hand coordination during (pre-adaptation) adaptation training, especially for those susceptible to the ill-effects of such (motion sickness).

While the above description contains many specificities, these should not be construed as limitations on the scope of the invention, but rather as an exemplification of one preferred embodiment thereof. Many other variations are possible. Accordingly, the scope of the invention should be determined not by the embodiment illustrated, but by the appended claims and their legal equivalents.

I claim:

1. A light weight optical system for transporting images viewed by a wearer so as to induce at least one symptom of motion sickness, the system adapted to be worn on a wearer's head comprising:
   a single prism for transposing light to induce at least one symptom of motion sickness, the prism comprised of a lighter than glass material, the material having an optically flat surface measuring less than 40 waves so as to provide clear visual images;
   frame means for positioning the prism in front of both eyes of the wearer;
   light occluding means for preventing substantially all untransposed light from entering the eyes of the wearer; and,
   means for securing said optical system to the wearer's head, said system being sufficiently light weight to allow the wearer to wear it for a prolonged period of time and without the need for counter-weights.

2. The optical system of claim 1 wherein the prism is 45°×45°×90° prism, wherein the prism is oriented such that the hypotenuse is perpendicular to the plane which contains both of said eyes of the wearer and such that apex of the hypotenuse forms a line oriented parallel to the plane which contains both of the eyes.

3. The optical system of claim 1 wherein the lighter than glass material comprises a transparent polymer.

4. The optical system of claim 3 wherein the transparent polymer comprises an acrylic polymer.

5. The optical system of claim 1 wherein the prism comprises a nose notch, whereby the surface of the prism can be held closer to the eyes of the wearer when the bridge of the nose of the wearer is positioned within the nose notch of the prism.

6. The optical system of claim 1 wherein the frame means further comprises a plurality of vents for allowing air to circulate around the eyes and the prism, whereby fogging of the prism is minimized.

7. The optical system of claim 6 wherein the light occluding means includes opaque porous covering means for blocking untransposed light from passing through said vents.

8. The optical system of claim 1 wherein the length of said prism is greater than the distance between said eyes of said wearer, whereby both eyes of said wearer can look through said prism at the same time.

9. The optical system of claim 1 wherein the means for securing the frame means comprises a strap comprised of a length of flexible material and means for adjusting the length of the flexible material.

10. The optical system of claim 1 wherein the frame means further comprises means for easily removing the prism from the frame.

11. The optical system of claim 1 wherein the frame means further comprises housing means for covering at least one side of the prism, whereby light is blocked from entering at least one side of said prism.

12. The optical system of claim 1 wherein the frame means further comprises face seal means for blocking untransposed light from entering the eyes of the wearer by adapting to the contours of the face of the wearer.

13. A light weight optical system for transporting images viewed by a wearer so as to induce at least one symptom of motion sickness, the system adapted to be worn on the wearer's head, comprising:
   a single unitary prism for transporting light so as to induce at least one symptom of motion sickness, the prism comprised of a lighter than glass material, the material having an optically flat surface measuring less than 40 waves so as to provide a clear visual image;
   a goggles frame adapted to receive the prism and position the prism in front of the eyes of the wearer; and
   light occluding means affixed to the goggles frame for preventing substantially all untransposed light from entering the eyes of the wearer said prism being light enough to allow the wearer to wear it for a prolonged period of time and without the need for counter-weights.

14. The optical system of claim 13 wherein the prism is 45°×45°×90° prism, wherein the prism is oriented such that the hypotenuse is perpendicular to the plane which contains both of said eyes of the wearer and such that apex of the hypotenuse forms a line oriented parallel to the plane which contains both of the eyes.

15. The optical system of claim 13 wherein the lighter than glass material comprises a transparent polymer.

16. The optically system of claim 15 Wherein the transparent polymer comprises an acrylic.

17. The optical system of claim 13 wherein the prism comprises a nose notch, whereby the surface of the prism can be held closer to the eyes of the wearer when the bridge of the nose of the wearer is positioned within the nose notch of the prism.

18. The optical system of claim 13 wherein the frame means further comprises a plurality of vents for allowing air to circulate around the eyes and the prism, whereby fogging of the prism is minimized.

19. The optical system of claim 18 wherein the light occluding means includes opaque porous covering means for blocking untransposed light from passing through said vents.

20. The optical system of claim 13 wherein the length of said prism is greater than the distance between said eyes of said wearer, whereby both eyes of said wearer can look through said prism at the same time.

21. The optical system of claim 13 wherein the means for securing the frame means comprises a strap comprised of a length of flexible material and means for adjusting the length of the flexible material.

22. The optical system of claim 13 wherein the frame means further comprises means for easily removing the prism from the frame.

23. The optical system of claim 13 wherein the frame means further comprises housing means for covering at least one side of the prism, whereby light is blocked from entering at least one side of said prism.

24. The optical system of claim 13 wherein the frame means further comprises face seal means for blocking untransposed light from entering the eyes of the wearer by adapting to the contours of the face of the wearer.

25. The optical system of claim 1 wherein the optically flat surface measures less than about 20 waves.

26. The optical system of claim 13 wherein the optically flat surface measures less than about 20 waves.

* * * * *